(12) United States Patent
Hamilton

(10) Patent No.: US 6,791,092 B2
(45) Date of Patent: Sep. 14, 2004

(54) TRANSMISSION METER, A METHOD OF MEASURING TRANSMITTANCE AND A DISINFECTION APPARATUS

(75) Inventor: David John Hamilton, Slough (GB)

(73) Assignee: Hanovia Limited (GB)

( * ) Notice: Subject to any disclaimer, the term of this patent is extended or adjusted under 35 U.S.C. 154(b) by 192 days.

(21) Appl. No.: 09/794,728

(22) Filed: Feb. 27, 2001

(65) Prior Publication Data

US 2001/0046461 A1 Nov. 29, 2001

(30) Foreign Application Priority Data

Mar. 3, 2000 (EP) .............................. 00301783

(51) Int. Cl.$^7$ .................................................. G01J 1/08
(52) U.S. Cl. ....................... 250/373; 250/343; 250/372
(58) Field of Search ................................. 250/373, 343, 250/372, 336.1, 338.1, 305

(56) References Cited

U.S. PATENT DOCUMENTS

| 4,017,734 | A | * | 4/1977 | Ross ........................... 250/431 |
| 4,204,956 | A | * | 5/1980 | Flatow ......................... 210/87 |
| RE34,513 | E | * | 1/1994 | Ellner ...................... 250/432 R |
| 5,629,212 | A | | 5/1997 | Herman et al. .............. 436/125 |
| 6,264,836 | B1 | * | 7/2001 | Lantis ......................... 210/188 |
| 2002/0066874 | A1 | * | 6/2002 | Drescher ................ 250/504 R |

FOREIGN PATENT DOCUMENTS

| DE | 19824423 | | 12/1999 | ............. C02F/1/32 |
| JP | 10057954 | | 3/1998 | ............. C02F/1/32 |
| JP | 11-226467 | * | 2/2001 | ............. C02F/1/32 |
| NL | 1003961 | | 3/1998 | ........... G01B/21/59 |

* cited by examiner

Primary Examiner—David Porta
Assistant Examiner—Christine Sung
(74) Attorney, Agent, or Firm—Schwegman, Lundberg, Woessner & Kluth, P.A.

(57) ABSTRACT

A transmission meter (1) and a method for measuring the transmittance of a fluid, the meter (1) comprises an analysis chamber for passage of the fluid therethrough, means for receiving an electromagnetic source (9) within said chamber and three sensors (D1, D2 and D3) each configured to measure the output from said source (9), wherein each of the three sensors (D1, D2 and D3) are located at different distances from the source (9). The transmission meter may be used in a disinfection system either to measure the transmittance of the untreated water or to measure the transmittance of the water as it is purified.

19 Claims, 3 Drawing Sheets

TRANSMISSION METER, A METHOD OF MEASURING TRANSMITTANCE AND A DISINFECTION APPARATUS

FIELD OF THE INVENTION

The present invention relates to the field of transmission meters and methods for measuring the transmittance of fluids. More specifically, the present invention relates to a transmission meter and method for measuring the transmittance of a fluid, such as water, in a sterilisation or disinfection apparatus.

BACKGROUND OF THE INVENTION

Ultraviolet (UV) disinfection equipment works by irradiating the fluid to be purified, with radiation having wavelengths predominantly in the range from 240 to 280 nm. Such UV disinfection equipment has many uses such as treating the domestic and public water supplies, water supplies for the process industry, sewage effluent, and any applications where the presence of pathogens may be injurious to health. Therefore, satisfactory disinfection must be achieved in order to safeguard the health of the public.

To achieve satisfactory disinfection of the liquid, it is important to know the rate of fluid flow, the UV intensity within the disinfection chamber and the fluid transmittance at the wavelength of the UV radiation. Knowing the above will allow the performance of the disinfection equipment to be continuously monitored, and, if necessary, corrective action can be taken if the levels fall below predefined limits.

The flow rate can be easily measured by well known techniques. The UV intensity within the disinfection or purification chamber can also be measured by placing a UV sensor in the chamber. The transmittance of a fluid is generally measured by placing a radiation source in the fluid to be measured and measuring the intensity of the detected radiation at a point distant from the source. The transmittance can be easily calculated if the power of the source, the distance of the detector from the source is known and that there is no other obstruction between the source and the detector.

The problem arises when the sensor is required to monitor the transmittance of a continuously or intermittently flowing fluid over a long time, for example, a few days, weeks, months, even years. A single UV sensor will be able to sense a decrease in the intensity of the light from the UV source over time. However, it will not be able to establish if this is due to the output of the source decreasing over time or, the transmittance of the fluid itself changing. Another factor which will affect the measured intensity is so-called photochemical fouling which occurs due to the fluid depositing particles, especially iron and manganese compounds, on the source and optic surfaces of the sensor.

Previous attempts to address the above problems have included a meter with a detector which is moveable between two positions as described in NL1003961 and a meter with two fixed detectors at different distances from the source as described in JP 10057.

SUMMARY OF THE INVENTION

A first aspect of the present invention provides a transmission meter for measuring the transmittance of a fluid, the meter comprising:

a chamber for the flow of fluid therethrough and adapted to receive
an electromagnetic source within said chamber; and
three sensors each configured to measure the output from said source,
wherein each of the three sensors are located at different distances from the source.

The three sensors allow detection of the intensity of the emitted radiation at three different points. The intensity detected at each of the sensors will be dependent on the irradiance of the source, the transmittance of the fluid, the distance of the source from the sensor and the extent of deposition on the optic surfaces of the apparatus. As the distance of each of the sensors from the source is known, it is possible to establish the transmittance of the fluid. More than three sensors could be used if required.

Preferably, the sensors all measure the irradiance from the same part of the source. This eliminates errors due to the irradiance of the source varying across its output surface and variations in photochemical fouling of the source. To obtain accurate readings, it is preferable if the sensors are at significantly different distances from the source. For example, preferably, the distances of the two sensors which are furthest from the source are substantially integral multiples of the distance of the closest sensor to the source.

As previously mentioned, the meter is primarily intended for use in a disinfection apparatus. Therefore, in a second aspect, the present invention provides a disinfection apparatus comprising a transmission meter and a purification chamber, said purification chamber being capable of receiving an electromagnetic source for purifying fluid passing through said purification chamber, said meter comprising an analysis chamber for passage of the fluid therethrough, means for receiving an electromagnetic source within said analysis chamber and three sensors each configured to measure the output from said source within the analysis chamber, wherein each of the three sensors are located at different distances from the source.

Preferably, the transmission meter is located upstream from the purification chamber. Thus, it is used to measure the transmittance of the fluid prior to treatment. This can be achieved by directing a fraction of the fluid in the inlet pipe to the purification chamber into the transmission meter.

In many instances, there will be more than one purification chamber. The plurality of purification chambers will preferably be provided in a parallel arrangement as opposed to a series arrangement.

The data collected by the three sensors in the analysis chamber can be analysed remote from the meter. For example, the sensors could each have means to transmit the data from the meter to a remote analyser, or, the meter could be provided with data storage means for periodic collection by a computer via a hardwire or wireless link or even manually by an operator.

Alternatively, the meter may comprise analysis means to compare the output of the three sensors. The analysis means could output an electrical signal which is related to the transmittance of the fluid. This electrical signal could either be analogue or digital in character.

Preferably, the meter or the disinfection system comprises a controller into which the output from the analysis means is fed. The controller may be used to control the meter to perform calibration or self cleaning functions. Alternatively, the controller may be used to adjust the parameters of the purification chamber to maintain treatment levels within acceptable limits. Typically, there is a predefined minimum level for the treatment level of the chamber.

For example, the controller could be used to increase the power supplied to the radiation source or sources within the purification chamber. In the case where there are many purification chambers provided in parallel, the controller can be used to bring on line or switch fluid away from one or more of the chambers i.e. it can be used to control the number of chambers in use at any one time.

The knowledge of the transmittance of the fluid allows the level of treatment required by the fluid to be accurately computed.

To perform the cleaning and/or calibration functions, the meter preferably further comprises valve means configured to switch the supply of fluid into the chamber between at least two different sources. The two sources are preferably a source containing the fluid which is to be measured and a source containing de-ionised water which has virtually 100% transmission at UV wavelengths. UV wavelengths are typically between 200 nm and 400 nm, and more specifically from 240 nm to 280 nm.

More preferably, the meter further comprises at least one valve which is capable of switching between three sources. The sources are preferably, the fluid which is to be treated, a de-ionised water source and a source of weak acid. The weak acid supply is used to clean the chamber. The weak acid may be a dilute phosphoric acid, for example, a solution containing about 5% phosphoric acid by volume, or it could be another acid for example hydrochloric acid at a similar strength. The valve means could also be configured to switch the supply between just untreated fluid and weak acid.

Preferably, the source chosen by the valve means is controlled by the control means.

Providing the transmission meter with an inlet which can be switched between two or more supplies allows the transmission meter to be cleaned, calibrated etc without the need to disassemble the system. Therefore, in a third aspect, the present invention provides a meter for measuring a fluid, the meter comprising a chamber for the passage of fluid therethrough, at least one sensor for detecting a parameter within the chamber and means for switching the type of fluid which flows through the chamber dependent on the parameter detected by at least one sensor.

The sensed parameter can be the fluid transmittance, the irradiation from a radiation source located within the chamber etc. The different types of fluid may be chosen from the fluid which is to be measured in the chamber, a reference fluid, (for example, pure water), which can be used to calibrate the system or a cleaning fluid (for example, an acid). The meter can be used to measure any property of the fluid, for example, the transmittance, flow rate etc.

Preferably, the purification chamber also comprises cleaning means for cleaning the chamber. These cleaning means may be provided by a mechanical system which operates on a fixed time cycle. These cleaning means may be controlled by software which is used to detect when the UV level within the chamber falls below a certain limit. These cleaning means may also be controlled by the control means.

Preferably, the apparatus further comprises a flow meter such that the rate of fluid flow through the purification chamber and the transmission meter can be monitored.

Above, the disinfection apparatus has been described as having two chambers, an analysis chamber and a purification chamber. However, the analysis of the transmittance of the fluid under treatment could be performed within the purification chamber.

Therefore, in a fourth aspect the present invention provides a disinfection apparatus comprising a purification chamber adapted to receive an electromagnetic source for purifying liquid passed through said purification chamber, the apparatus further comprising three sensors each configured to measure the output from said source, wherein each of the three sensors are located at different distances from the source.

Typically, the purification chamber will have a plurality of sources. Preferably, to obtain consistent results, the three sensors will measure the output from the same electromagnetic source. Even more preferably, from the same part of the source.

In a fifth aspect, the present invention provides a method for measuring the transmittance of a fluid, the method comprising the steps of:

passing the fluid between an electromagnetic source and three sensors configured to measure the output from said source, wherein each of the sensors are located at different distances from said source; and measuring the output of the source using each of the three sensors.

The present invention will now be described with reference to the following preferred non-limiting embodiments.

DESCRIPTION OF THE PREFERRED EMBODIMENT

Figure 1:
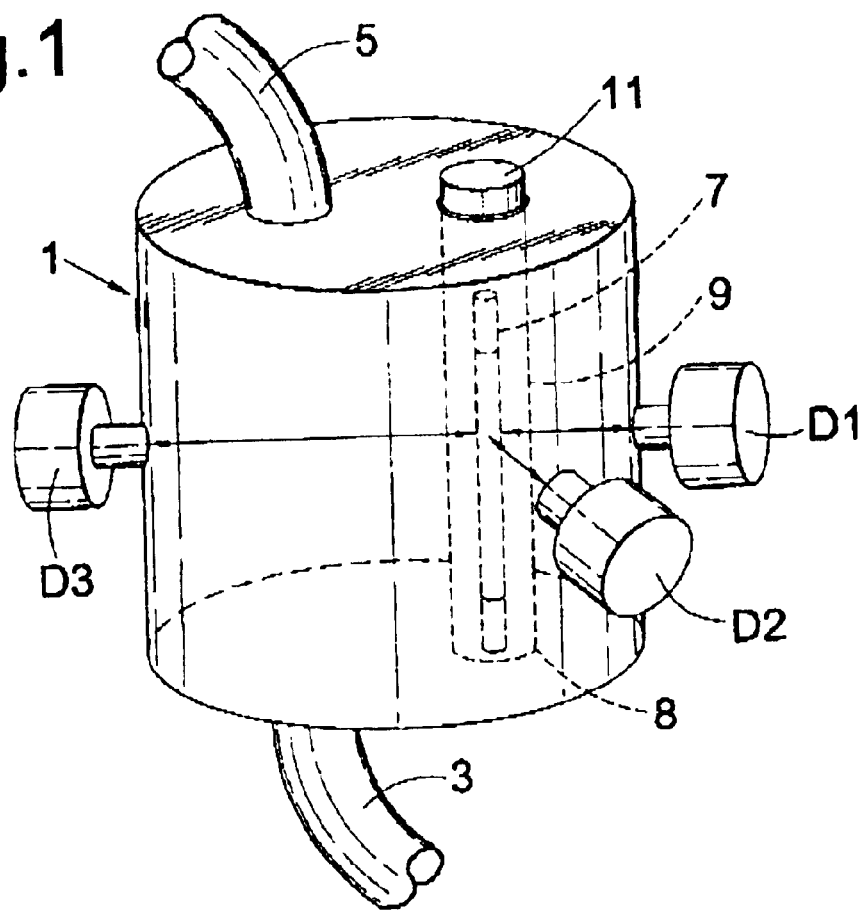
FIG. 1 shows a transmission meter in accordance with an embodiment of the present invention.

The transmission meter of FIG. 1 has a cylindrical chamber 1 through which the fluid to be treated is passed. The fluid will typically be water, but other fluids could be used. The fluid can flow through the chamber 1 either continuously or intermittently. The chamber 1 has an inlet pipe 3 and an outlet pipe 5 to allow the flow of fluid through the chamber 1. The outlet pipe 5 is situated on the upper side of the chamber 1 as this avoids problems due to trapped air. The chamber 1 is made from a corrosion resistant material such as stainless steel and is designed to withstand the maximum pressure to which the meter will be connected. The diameter of the chamber will typically be about 0.2 m.

An elongate fused silica sleeve 9 is located within the chamber 1. The sleeve 9 is orientated parallel to the central symmetry axis of the cylindrical chamber, and to one side of the central axis.

The meter will ideally operate without maintenance for a period of about 12 months. Therefore, a suitable source which can operate under these conditions should be chosen.

The UV source used in most laboratory spectrophotometers is a Deuterium lamp which has a stable continuous output between 200 nm and 400 nm. These lamps tend to be expensive and have a short operating time of between 1000 to 2000 hours. The preferred source is a low pressure mercury discharge lamp. These emit a spectral line at 253.7 nm. These are low cost lamps with a long operating life. However, their output changes with temperature and time.

A UV source 7, which will typically be an 8-watt Sankyo Denki UV lamp, is located within the sleeve 9 to form a sleeve and source assembly 8. The lamp irradiates at 253.7 nm. The sleeve and source assembly 8 is inserted into chamber 1 via port 11 which is located on the outlet side 5 side of the chamber 11. The lamp 7 and sleeve 9 may be separated from each other. However, typically, the lamp and sleeve are a single assembly.

Three sensors, D1, D2 and D3 are located in a plane perpendicular to the symmetry axis of the chamber 1 and about the circumference of chamber 1. As the source 7 is placed off-centre in the chamber 1, each of the sensors is disposed at a different distance from the source 7.

Ideally, the transmittance of the fluid should be measured across the germicidal range which is from 240 nm to 280 nm. However, it is generally accepted that a measurement at 254 nm (which is consistent with the preferred UV source) is adequate.

Figure 2:
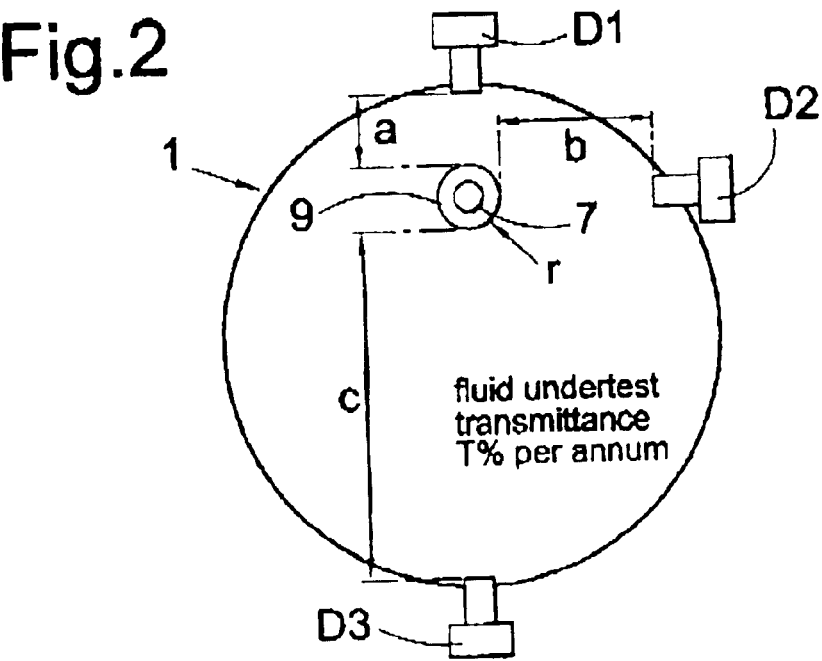
FIG. 2 shows a sectional view of the transmission meter of FIG. 1.

FIG. 2 shows a section through the cylindrical chamber 1, taken through the plane of the sensors D1, D2 and D3. Sensor D1 is closest to the source 7 and is at distance "a" away from the circumference of the sleeve 9. Sensor D2 is slightly further away from the source than sensor D1 and is at distance "b" from the sleeve 9. Sensor D3 is at distance "c" from the sleeve and is the furthest sensor from the source 7. The radius of the sleeve 9 is "r".

The distances a, b and c are determined by the exact position of the sensors on the circumference of the chamber and the position of the source 9 in the chamber. The source 9 and sensors D1, D2 and D3 will be arranged to allow a significant difference between distances a, b and c. Typically, b and c will be n multiples of a, where n is an integer of 2 or more. In a chamber with a diameter of about 0.2 m, a will be about 0.04 m, b will be about 0.08 m and c will be about 0.12 m.

The optimum lengths of distances a, b and c will depend, to a certain extent, on the transmissitivity of the fluid to be measured. In water of a reasonably high quantity, the smallest path length will be about 4 cm. In poor quality fluids, the smallest path length should ideally be about 1 cm. For example, for a fluid with a low transmissitivity, a, b and c will typically be 1 cm, 2 cm and 3 cm. This would require a chamber diameter of about 5 cm.

Assuming that the UV power which is outputted by the source is "P", the length of the UV source is "L", the transmittance of the fluid under test is "T % per meter" and that the attenuation due to deposition on optical surfaces is "K", the following simplified relations can be derived for the intensity of light H measured at sensors D1, D2 and D3

$$\text{Intensity at } D1 = H_1 = \frac{P}{2\pi L(a+r)} \cdot K \cdot T^a$$

$$\text{Intensity at } D2 = H_2 = \frac{P}{2\pi L(b+r)} \cdot K \cdot T^b$$

$$\text{Intensity at } D3 = H_3 = \frac{P}{2\pi L(c+r)} \cdot K \cdot T^c$$

By dividing the above 3 equations, it is possible to eliminate the non-linear term "K":

$$\frac{H_2}{H_1} = \frac{(a+r)}{(b+r)} \cdot T^{(b-a)}$$

$$\frac{H_3}{H_1} = \frac{(a+r)}{(c+r)} \cdot T^{(c-a)}$$

$$\frac{H_3}{H_2} = \frac{(b+r)}{(c+r)} \cdot T^{(c-b)}$$

a, b and c are easily measurable. For this example, it will be assumed that b=2a and c=3a. In this situation, the following equations are derived:

$$T^{(a)} = \frac{H_2}{H_1} \cdot \frac{(2a+r)}{(a+r)} = \frac{H_2}{H_1} \cdot k_1$$

$$T^{(a)} = \sqrt{\frac{H_3}{H_1} \cdot \frac{(3a+r)}{(a+r)}} = \sqrt{\frac{H_3}{H_1}} \cdot k_2$$

$$T^{(a)} = \frac{H_3}{H_2} \cdot \frac{(3a+r)}{(a+r)} = \frac{H_3}{H_2} \cdot k_3$$

where $k_1$, $k_2$ and $k_3$ are dimensionless constants.

From these calculations, it is seen that the transmittance of the fluid can be derived from three separate calculations using the intensity measurements $H_1$, $H_2$, $H_3$.

It is also evident that the three distances a, b, c should ideally be significantly different to enable the effects of attenuation due to deposition on the optical surfaces and variation of UV source output to be eliminated.

The above analysis has been simplified to illustrate how the transmittance of the fluid can be derived. In practice, the above equations for $H_1$, $H_2$, $H_3$ may contain a more complex algorithm, however any errors due to simplification are of second order and can be easily corrected in the remote analyser.

Figure 3:
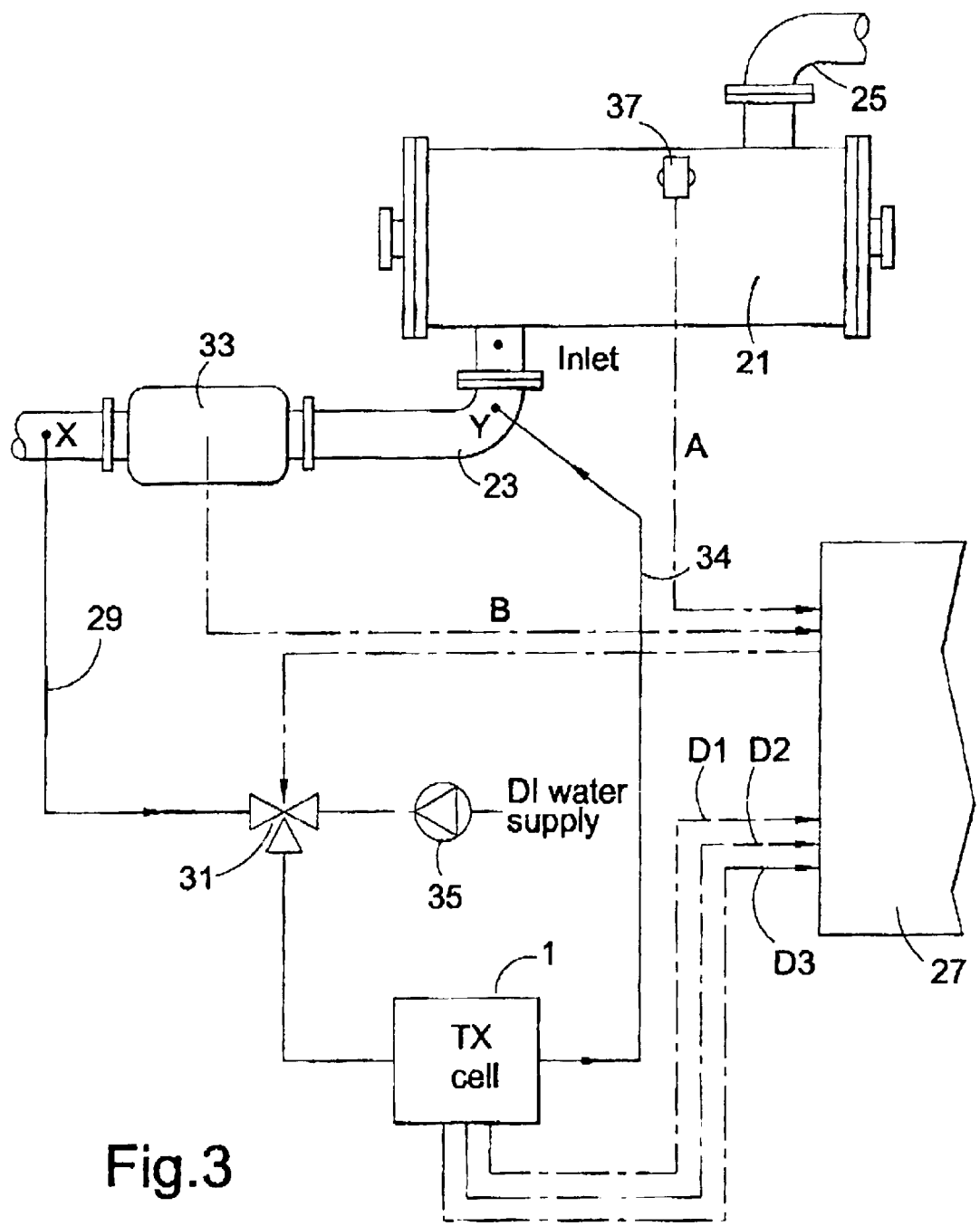
FIG. 3 shows a water disinfection system incorporating the embodiment of FIG. 1.

In practice, the transmission meter of FIG. 1 will be primarily used in combination with a water disinfection system such as that shown in FIG. 3. The meter will be placed upstream of the purification chamber, such that the transmittance of the water to be treated is measured.

The system comprises a purification chamber 21 which has an inlet pipe 23 and an outlet pipe 25 for ensuring the flow of water through the purification chamber 21. The inlet pipe 23 carries untreated water into the purification chamber 21. The purification chamber 21 comprises at least one UV light source similar to that described in relation to FIG. 1. The UV light source is used to purify the water. As a high power is required to disinfect the large volume of water in the chamber 21, there will often be a plurality of UV light sources in each purification chamber 21. Typically, the purification chamber 21 will be cylindrical with a diameter from 0.2 m to 0.5 m and a length from 1 m to 1.5 m.

The purification chamber will also have at least one UV sensor 37 (which is similar to sensors D1, D2 and D3). This will be described in more detail with reference to FIG. 5. The UV sensor 37 is used to measure the germicidal UV intensity within the purification chamber 21. Typically, a UV sensor will be provided for each UV source.

A flow meter 33 is provided on inlet pipe 23. The inlet 23 has a branch 29 located upstream from the flow meter 33 which takes untreated water to valve 31. Providing that valve 31 is set to an appropriate setting, the water from branch pipe 29 flows into transmission meter 1 for measurement.

Water which has passed through transmission meter 1 is taken back into the inlet pipe 23 by pipe 34. Pipe 34 joins the inlet pipe 23 upstream from the purification chamber 1, but downstream from flow meter 33.

The disinfection apparatus comprises a control means provided by a processor 27. The processor is used to process data from the transmission meter 1, the purification chamber 21 and also data from flow meter 33. The processor 27 may take the output directly from sensors D1, D2 and D3 (as shown in the Figure). Alternatively, the output from sensors D1, D2 and D3 may be analysed prior to entering to processor 27 so that processor 27 receives a signal from the transmission meter 1 which is related to the transmittance of the fluid to be treated.

The processor 27 takes the output from the UV sensor 37 in the purification chamber 21 via input channel A and it takes the output from the flow meter 33 via input channel B. Using the data from these inputs and the data from the transmission meter 1, the processor can fully monitor the disinfection system. Further, the processor can be used to control various parts of the system depending on the data received.

In order to ensure that the correct treatment levels for the water are used, the processor 27 can increase the power supplied to the UV source within purification chamber 21. Often, a plurality of purification chambers 21 are provided in parallel. The inlet to each purification chamber has a value. The processor 27 controls these valves such that the number of purification chambers in use at any one time can be automatically controlled dependent on the inputs received by processor 27.

In FIG. 3 the flow of untreated water into the transmission meter 1 is controlled via valve 31. Valve 31 is connected to untreated water pipe 29, it is also connected to de-ionised water supply 35, such that the flow of fluid into the transmission meter 1 can be switched between untreated water and de-ionised water. De-ionised water has a transmittance of close to 100%. Therefore, switching the fluid supply to de-ionised water will allow the processor to send a command to re-calibrate the sensors of the transmission meter.

In FIG. 3, the processor 27 only has an output to valve 31. However, processor 27 can also be used to control a cleaning operation of the meter 1. This will be described in more detail with reference to FIG. 6. Further, the processor 27 could also be used to control the purification chamber itself For example, it could be used to instruct a cleaning operation of the chamber, or it could be used to reduce the flow of untreated water into the chamber 21 if the power of the UV sources are stating to decrease etc.

The processor can also be used to turn off the source of electromagnetic irradiation inside the meter 1, in order to set a zero reference for the three sensors D1, D2 and D3.

Figure 4:
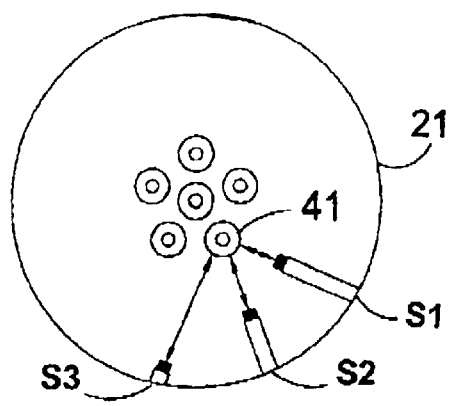
FIG. 4 shows a further embodiment of the present invention where the transmission meter is in-situ in a purification chamber.

In the arrangement of FIG. 3, the meter is separate from the purification chamber 21. In FIG. 4, the transmission meter 1 is provided in-situ in the purification chamber 21. Sensors S1, S2 and S3 are located around the circumference of the purification chamber 21 and at different distances from source 41. The same calculation can thus be carried out by taking the readings from sensors S1, S2 and S3 as explained in relation to FIGS. 1 and 2.

Figure 5:
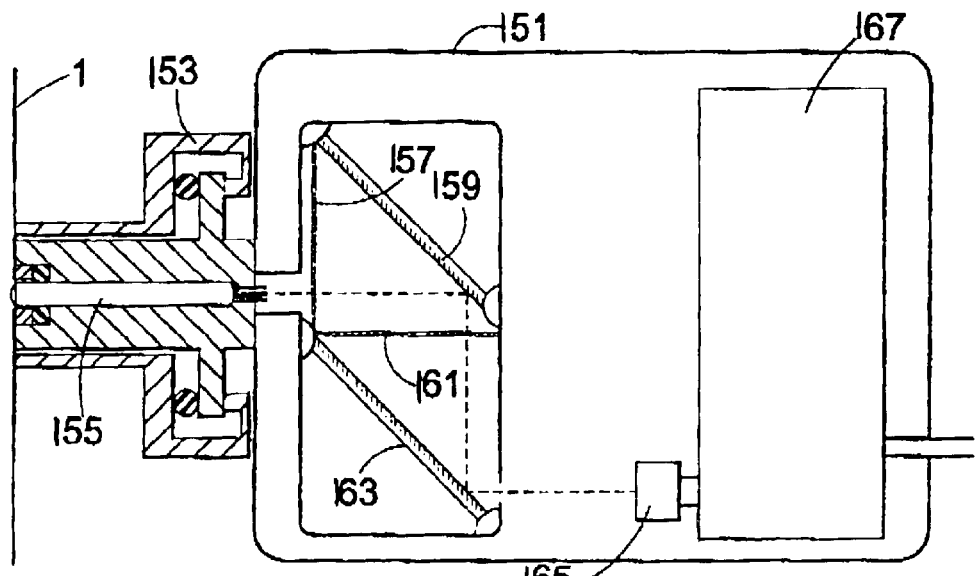
FIG. 5 shows an example of a sensor which may be used in accordance with an embodiment of the present invention.

FIG. 5 is a schematic of a preferred sensor assembly which can be used for sensors D1 to D3 or sensor 37 on the purification chamber. The sensor has a main body 151 and a connecting collar 153. The connecting collar 153 is used to connect the sensor to the side of chamber 1 or purification chamber 21.

UV light from the source inside the chamber 1,21 is detected by fused silicon probe 155 which is located within connection collar 153. The output from the fused silicon probe 155 is passed through an attenuation filter 157 and onto first mirror 159 which is located with the body 151 of the sensor. First mirror 159 has a coating which allows the mirror to only reflect light within a certain wavelength range. The reflected light is then passed through a second attenuating filter 161.

The light which passes through filter 161 is reflected off second mirror 163 which is also configured only to reflect light within a certain wavelength range. Typically, the wavelength range for both of the first and second mirrors will be from 240 to 280 nm. The light is then reflected onto photo-diode 165 which outputs an electric signal dependent on the intensity of radiation incident on the photo-diode. The electric signal is then fed into signal box 167 for amplification and conditioning of the signal. The electrical signal is then fed out of main body 151. The signal may be analogue or digital.

Figure 6:
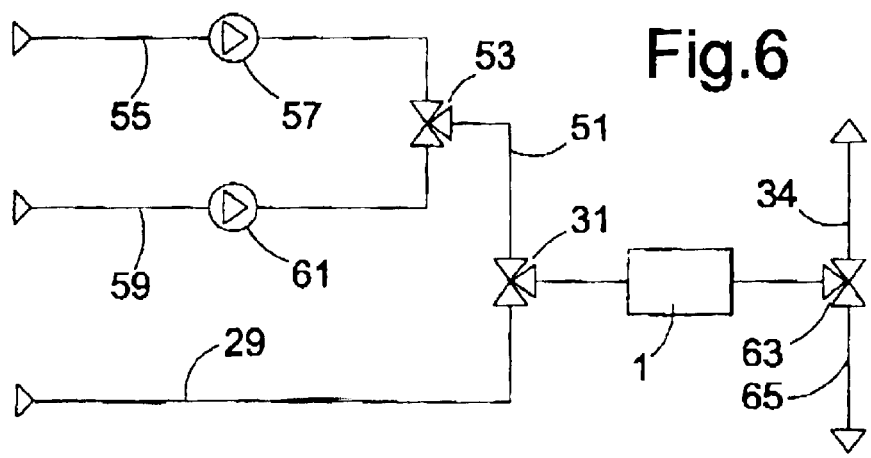
FIG. 6 shows a valve arrangement in accordance with a preferred embodiment of the present invention.

As has previously been mentioned, the processor 27 can be used to control the cleaning of the transmission meter 1. A possible arrangement for achieving this is shown in FIG. 6. To avoid unnecessary repetition, like numerals from FIG. 3 will be used to denote like features in FIG. 6.

Untreated water is fed through branch pipe 29 to valve 31. If valve 31 is open to line 29 then untreated water will be fed into the transmission meter 1 as described with reference to FIG. 3. If valve 31 is not open to line 29 but is instead open to line 51, secondary valve 53 which is located on line 51 determines the type of fluid which will flow into the transmission meter 1. Secondary valve 53 can either allow dilute acid to pass from line 55 through pump 57 into valve 53 and hence into the transmission meter 1 via valve 31 and line 51. Or, valve 31 may allow de-ionised water from line 59 through pump 61 to pass into the transmission meter 1. The dilute acid can be used to clean the system as it will dissolve much of the scale which will accumulate within the transmission meter. The water can then be used to re-calibrate the system as previously described.

Once the water has passed through the transmission meter 1, it is fed into outlet valve 63. Outlet valve 63 will either let the fluid be passed back into line 34 and hence into inlet pipe 23. Alternatively, valve 63 can direct water or dilute acid down line 65 into the drain. If the transmission meter 1 is being washed with acid, obviously, it is desirable if the valve 63 directs the acid into the drain.

What is claimed is:

1. A transmission meter for measuring the transmittance of a fluid, the meter comprising an analysis chamber for passage of the fluid therethrough and adapted to receive an electromagnetic source within said chamber, wherein the meter further comprises three sensors each configured to measure the output from said source, wherein each of the three sensors are located at different distances from the source.

2. The meter of claim 1, further comprising analysis means for comparing the outputs from each of the sensors to determine the transmittance of the fluid.

3. The meter of claim 1, wherein the sensors are arranged to detect the output from a same part of an output surface of the said source.

4. The meter of claim 1, wherein the distances of the two sensors which are furthest from the source are substantially integral multiples of the distance of the closest sensor to the source.

5. The meter of claim 1, further comprising a valve configured to switch the supply of fluid to the analysis chamber between at least two fluid supply lines.

6. The meter of claim 5, wherein the valve is configured to switch the supply between at least three different fluid supply lines.

7. The meter of claim 5, wherein at least one of the fluid supply lines is a de-mineralised water source for calibration of the meter.

8. The meter of claim 5, wherein at least one of the fluid supply lines is an acid source for cleaning the transmission meter.

9. The meter of claim 5, the meter further comprising a controller for determining the supply of fluid into the analysis chamber.

10. A disinfection apparatus comprising a meter according to claim 1, and a purification chamber, said purification chamber being capable of receiving an electromagnetic source for purifying liquid passed through said purification chamber.

11. The apparatus of claim 10, wherein the fluid which is to be purified is fed into the purification chamber via an inlet pipe and a fraction of the fluid in this pipe is fed into the analysis chamber.

12. The apparatus of claim 11, wherein fluid which exits the analysis chamber is fed back into the said inlet pipe.

13. The apparatus of claim 10, wherein a further UV sensor is located in said purification chamber.

14. The apparatus of claim 10, wherein the apparatus further comprises a flow meter for measuring the flow of fluid into the purification chamber.

15. The apparatus of claim 10, wherein the output from the sensors is fed into a controller and said controller is capable of initiating corrective action in said purification chamber.

16. A disinfection apparatus comprising a purification chamber adapted to receive an electromagnetic source for purifying fluid passed through said purification chamber, characterised in that the apparatus further comprises three sensors each configured to measure the output from said source, wherein each of the three sensors are located at different distances from a source in said purification chamber.

17. The disinfection apparatus of claim 16, wherein a first sensor of the three sensors is located at a first distance from the source, a second sensor of the three sensors is located at a second distance from the source, a third sensor of the three sensors is located at a third distance from the source, and wherein the first and second distances are substantially integral multiples of the third distance.

18. A method for measuring the transmittance of a fluid, comprising:

passing the fluid between an electromagnetic source and three sensors configured to measure the output from said source, wherein each of the sensors are located at different distances from said source; and measuring the output of the source using each of the three sensors.

19. The method of claim 18, wherein measuring the output includes measuring the transmittance of the fluid over three different distances between the source and each of the three sensors.

* * * * *